United States Patent
Kim et al.

(10) Patent No.: US 10,815,293 B2
(45) Date of Patent: Oct. 27, 2020

(54) METHOD FOR PURIFYING FIBRINOGEN (71) Applicant: GREEN CROSS HOLDINGS CORPORATION, Yongin-si, Gyeonggi-do (KR)

(72) Inventors: Jun Sic Kim, Yongin-si (KR); Hyo Jin Kim, Yongin-si (KR); Ji Yoon Park, Yongin-si (KR); Ju Ho Lee, Yongin-si (KR); Jae Woon Son, Yongin-si (KR); Yong Won Shin, Yongin-si (KR)

(73) Assignee: GREEN CROSS HOLDINGS CORPORATION, Yongin-si (KR)

( * ) Notice: Subject to any disclaimer, the term of this patent is extended or adjusted under 35 U.S.C. 154(b) by 0 days.

(21) Appl. No.: 15/781,737

(22) PCT Filed: Jan. 12, 2017

(86) PCT No.: PCT/KR2017/000389
§ 371 (c)(1),
(2) Date: Jun. 6, 2018

(87) PCT Pub. No.: WO2017/123012
PCT Pub. Date: Jul. 20, 2017

(65) Prior Publication Data
US 2018/0362615 A1   Dec. 20, 2018

(30) Foreign Application Priority Data
Jan. 12, 2016 (KR) .......................... 10-2016-0003475

(51) Int. Cl.
*C07K 14/75* (2006.01)
*A61K 38/36* (2006.01)
*B01J 20/08* (2006.01)
*C07K 1/30* (2006.01)
*C07K 1/34* (2006.01)
*C07K 1/36* (2006.01)

(52) U.S. Cl.
CPC .............. *C07K 14/75* (2013.01); *A61K 38/36* (2013.01); *B01J 20/08* (2013.01); *C07K 1/30* (2013.01); *C07K 1/34* (2013.01); *C07K 1/36* (2013.01)

(58) Field of Classification Search
None
See application file for complete search history.

(56) References Cited

U.S. PATENT DOCUMENTS

| | | |
|---|---|---|
| 4,188,318 A | 2/1980 | Shanbrom |
| 4,210,580 A | 7/1980 | Amrani |
| 4,764,369 A | 8/1988 | Neurath et al. |
| 5,639,940 A | 6/1997 | Garner et al. |
| 5,773,033 A | 6/1998 | Cochrum et al. |
| 6,037,457 A | 3/2000 | Lord |
| 6,277,961 B1 * | 8/2001 | Hock ............ A61K 38/45  530/382 |
| 7,442,308 B2 | 10/2008 | Ristol Debart et al. |
| 2004/0110686 A1 | 6/2004 | Clark et al. |

FOREIGN PATENT DOCUMENTS

| | | |
|---|---|---|
| CN | 104231072 A | 12/2014 |
| EP | 0 383 234 B1 | 11/1994 |
| EP | 0 408 029 B1 | 5/1995 |
| EP | 1057490 A2 | 12/2000 |
| KR | 10-2006-0043134 A | 5/2006 |
| KR | 10-2013-0112031 A | 10/2013 |
| WO | 95/25748 A1 | 9/1995 |
| WO | 99/37680 A1 | 7/1999 |
| WO | 01/48016 A1 | 7/2001 |
| WO | 2012/038410 A1 | 3/2012 |
| WO | 2013135684 A1 | 9/2013 |

OTHER PUBLICATIONS

E. Jakobsen et al., "A Modified Beta-Alanine Precipitation Procedure to Prepare Fibrinogen Free of Antithrombin-III and Plasminogen," Thrombosis Research, 1973, pp. 145-159, vol. 3, No. 2.
Y. Takeda, "Studies of the Metabolism and Distribution of Fibrinogen in Healthy Men with Autologous $^{125}$I-labeled Fibrinogen," Journal of Clinical Investigation, 1966, pp. 103-111, vol. 45, No. 1.
V. Vila et al., "A Rapid Method for Isolation of Fibrinogen from Human Plasma by Precipitation with Polyethylene Glycol 6,000," Thrombosis Research, 1985, pp. 651-656, vol. 39.
Wolfgang Jilg et al., "Isolation of Residual Fibrinogen from a Supernatant of Plasma Precipitated with 2.1 M Glycine," Thrombosis Research, 1976, pp. 479-489, vol. 9, No. 5.
International Search Report of PCT/KR2017/000389 dated Apr. 17, 2017.
Birger Blomback et al., "Purification of bovine and human fibrinogen", Acta Chemica Scandinavia, vol. 10, No. 1, Jan. 1, 1956, XP055603659, p. 147.

(Continued)

Primary Examiner — Marsha Tsay
(74) Attorney, Agent, or Firm — Sughrue Mion, PLLC (57) ABSTRACT

A method for purifying fibrinogen includes steps of: (a) precipitating fibrinogen of a fibrinogen-containing solution by adding glycine to the solution for a concentration of glycine to be 1.5 to 2.5M, and then removing a supernatant and recovering a precipitate ($1^{st}$ glycine precipitation); (b) dissolving the precipitate of $1^{st}$ glycine precipitation of step (a) in a dissolution buffer to obtain a solution, precipitating the solution by adding glycine thereto for a concentration of glycine to be 0.2 to 1.2M, and recovering a supernatant ($2^{nd}$ glycine precipitation); (c) precipitating the supernatant of step (b) by adding glycine thereto for a concentration of glycine to be 1.5 to 2.5M, and recovering a precipitate ($3^{rd}$ glycine precipitation); and (d) dissolving the precipitate of step (c) in a dissolution buffer to obtain a solution, and subjecting the solution to nanofiltration using a nanofilter.

13 Claims, 5 Drawing Sheets

(56) References Cited

OTHER PUBLICATIONS

Masahiro Okuda et al., "A New Method of Purifying Fibrinogen with Both Biological and Immunological Activity from Human Plasma", Preparative Biochemistry and Biotechnology, vol. 33, No. 4, Nov. 4, 2003, X002792776, pp. 239-252 (16 pages total).
Communication dated Jul. 12, 2019, from the European Patent Office in application No. 17738641.4.

* cited by examiner

METHOD FOR PURIFYING FIBRINOGEN

CROSS REFERENCE TO RELATED APPLICATIONS

This application is a National Stage of International Application No. PCT/KR2017/000389 filed Jan. 12, 2017, claiming priority based on Korean Patent Application No. 10-2016-0003475, filed Jan. 12, 2016.

TECHNICAL FIELD

The present disclosure relates to a method for purifying fibrinogen, and more particularly, to a method for purifying fibrinogen, comprising the steps of: (a) precipitating fibrinogen of a fibrinogen-containing solution by adding glycine to the solution for a concentration of glycine to be 1.5 to 2.5M, and then removing a supernatant and recovering a precipitate ($1^{st}$ glycine precipitation); (b) dissolving the precipitate of $1^{st}$ glycine precipitation of step (a) in a dissolution buffer to obtain a solution, precipitating the solution by adding glycine thereto for a concentration of glycine to be 0.2 to 1.2M, and recovering a supernatant ($2^{nd}$ glycine precipitation); (c) precipitating the supernatant of step (b) by adding glycine thereto for a concentration of glycine to be 1.5 to 2.5M, and recovering a precipitate ($3^{rd}$ glycine precipitation); and (d) dissolving the precipitate of step (c) in a dissolution buffer to obtain a solution, and subjecting the solution to nanofiltration (NF) using a nanofilter.

BACKGROUND ART

Fibrinogen, also known as clotting factor I, plays a key role in haemostasis and wound healing. It is a glycoprotein synthesized in the liver with an apparent molecular weight of 340 kDa, and is composed of two dimers, each of them built of three pairs of non-identical polypeptide chains called Aα, Bβ and γ linked by disulfide bridges. It circulates in the blood stream at a concentration of approximately 150-400 µg/ml. Upon injury of blood vessels, blood platelets are activated and a plug is formed. Fibrinogen is involved in primary haemostasis by aiding cross-linking of activated platelets.

At the same time, activation of the clotting cascade is initiated. As the endpoint, fibrinogen is converted into fibrin by proteolytic release of fibrinopeptide A and, at a slower rate, fibrinopeptide B by thrombin. The soluble fibrin monomers are assembled to double stranded twisted fibrils. Subsequently, these fibrils are arranged in a lateral manner, resulting in thicker fibers. These fibers are then cross-linked by FXIIIa to a fibrin network, which stabilizes the platelet plug by interactions of the fibrin with activated platelets, resulting in a stable clot.

Disorders and Deficiencies

Congenital afibrinogenaemia is a rare bleeding disorder, where patients are suffering from inadequate clotting of the blood due to the lack or malfunction of fibrinogen. This disorder might lead to spontaneous bleeding or excessive bleeding after minor traumata or during interventional procedures.

Acquired deficiencies in fibrinogen are much more common than congenital afibrinogenaemia and may be induced by haemodilution or other events such as blood losses during surgery, traumata, disseminated intravascular coagulation (DIC) or sepsis.

Fibrinogen deficiencies can be corrected to normal fibrinogen levels of about 1.5-3 g/l in plasma by replacement therapy with intravenous infusion of fresh frozen plasma or cryoprecipitate. However, these treatments are afflicted with the risk of introduction of pathogens, e.g. viruses or prions, into a patient, and thus cause additional disorders. It is thus advisable to intravenously apply virus inactivated fibrinogen compositions to restore fibrinogen at physiological levels in a safe way.

Fibrinogen Purification

Human plasma contains a complex mixture of more than 100 proteins, with fibrinogen accounting for about 2% of the total amount of protein. Therefore, the purification and isolation of fibrinogen usually requires a plurality of steps, and diverse combinations are possible for these individual process steps.

One important component of the purification of fibrinogen from human plasma is conventionally precipitation. Known precipitation methods use amino acids such as glycine or alanine (see: European Patent No. EP0383234; International Publication No. WO2001/48016; Jakobsen & Kierulf, Thrombosis Research, 3:145-159, 1973), ammonium sulfate (see: U.S. Pat. Nos. 5,773,033; 6,037,457; Takeda, Y, Journal of Clinical Investigation, 45:103-111, 1966), polymers such as polyethylene glycol (PEG) (see: International Publication No. WO1995/25748; Vila et al., Thrombosis Research 39:651-656, 1985), ethanol (see: European Patent No. EP0408029 wherein fibrinogen is precipitated and separated from other plasma proteins with 5-10% ethanol; Blomback & Blomback, Arkiv For Kemi, 10:415-443, 1956), sulphated polysaccharides (SPS, e.g., heparin) (see: International Publication No. WO1999/37680; U.S. Pat. No. 4,210,580), and solutions of low ionic strength (see: U.S. Pat. No. 4,188,318).

Examples of the disclosed conventional technologies associated with glycine precipitation in human fibrinogen purification processes include a two-step glycine precipitation process which comprises removing impurities produced in a pasteurization process for removing pathogenic particles (e.g., virus) and concentrating fibrinogen (CSL Behring, 2009), and a three-step glycine precipitation process obtaining a fibrinogen precipitate by use of only high-concentration 1.5-1.7M glycine (For a reference: U.S. Pat. No. 7,442,308; Grifols, E S). However, it has not been reported yet that a glycine precipitate containing impurities and insoluble substances is removed by performing a precipitation process using glycine at a concentration which is 2 to 4 times lower than the concentration of glycine used in the above-described process, the recovered supernatant is precipitated with a high concentration of glycine, and the recovery rate of high-purity fibrinogen is increased by improving the efficiency of nanofiltration, when a fibrinogen solution containing the precipitate dissolved therein is nanofiltered.

Under this technical background, the present inventors have made extensive efforts to develop a method for purifying fibrinogen, comprising the steps of: (a) precipitating fibrinogen of a fibrinogen-containing solution by adding glycine to the solution for a concentration of glycine to be 1.5 to 2.5M, and then removing a supernatant and recovering a precipitate ($1^{st}$ glycine precipitation); (b) dissolving the precipitate of $1^{st}$ glycine precipitation of step (a) in a dissolution buffer to obtain a solution, precipitating the solution by adding glycine thereto for a concentration of glycine to be 0.2 to 1.2M, and recovering a supernatant ($2^{nd}$ glycine precipitation); (c) precipitating the supernatant of step (b) by adding glycine thereto for a concentration of glycine to be 1.5 to 2.5M, and recovering a precipitate ($3^{rd}$ glycine precipitation); and (d) dissolving the precipitate of step (c) in a dissolution buffer to obtain a solution, and subjecting the solution to nanofiltration (NF) using a nanofilter, the efficiency of filtration increases at least 2-fold, so that high-purity fibrinogen from which virus was removed can be recovered, thereby completing the inventions of the present disclosure.

DISCLOSURE OF INVENTION

Technical Problem

It is an object of the present disclosure to provide a method for purifying high-purity fibrinogen, which can increase the efficiency of nanofiltration.

Technical Solution

To achieve the above object, the present disclosure provides a method for purifying fibrinogen, comprising the steps of: (a) precipitating fibrinogen of a fibrinogen-containing solution by adding glycine to the solution for a concentration of glycine to be 1.5 to 2.5M, and then removing a supernatant and recovering a precipitate ($1^{st}$ glycine precipitation); (b) dissolving the precipitate of $1^{st}$ glycine precipitation of step (a) in a dissolution buffer to obtain a solution, precipitating the solution by adding glycine thereto for a concentration of glycine to be 0.2 to 1.2M, and recovering a supernatant ($2^{nd}$ glycine precipitation); (c) precipitating the supernatant of step (b) by adding glycine thereto for a concentration of glycine to be 1.5 to 2.5M, and recovering a precipitate ($3^{rd}$ glycine precipitation); and (d) dissolving the precipitate of step (c) in a dissolution buffer to obtain a solution, and subjecting the solution to nanofiltration (NF) using a nanofilter.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

The terms "process", "purification", "separation" and "isolation", as used interchangeably herein, refer to the use of at least one method or system to achieve a specific purpose (for example, fibrinogen purification) in a purification process.

In one aspect, the present disclosure is directed to a method for purifying fibrinogen, comprising the steps of: (a) precipitating fibrinogen of a fibrinogen-containing solution by adding glycine to the solution for a concentration of glycine to be 1.5 to 2.5M, and then removing a supernatant and recovering a precipitate ($1^{st}$ glycine precipitation); (b) dissolving the precipitate of $1^{st}$ glycine precipitation of step (a) in a dissolution buffer to obtain a solution, precipitating the solution by adding glycine thereto for a concentration of glycine to be 0.2 to 1.2M, and recovering a supernatant ($2^{nd}$ glycine precipitation); (c) precipitating the supernatant of step (b) by adding glycine thereto for a concentration of glycine to be 1.5 to 2.5M, and recovering a precipitate ($3^{rd}$ glycine precipitation); and (d) dissolving the precipitate of step (c) in a dissolution buffer to obtain a solution, and subjecting the solution to nanofiltration (NF) using a nanofilter.

Unlike conventional process comprising a step of obtaining a precipitate from a precipitation process using glycine, the method for purifying fibrinogen according to the present disclosure, which comprises a precipitation process performed using glycine at a relatively low concentration, and then the supernatant, but not the precipitate, is recovered and nanofiltered, makes it possible to obtain fibrinogen with very high purity. Specifically, the fibrinogen purification method according to the present disclosure has effects in that the use of the inventive method increases the filtration efficiency of a nano-filter by more than twice to exhibit a high fibrinogen recovery with a purity of 98%, and the precipitation processes are performed using glycine at lowered concentrations so that impurities produced in the virus inactivation process can be removed as well as the filtration efficiency of the nano-filter can be increased as shown in Table 2 and FIGS. 3 to 8.

In an embodiment, the glycine concentration in the $1^{st}$ glycine precipitation in step (a) is 1.5 to 2.5M, preferably 1.8 to 2.2M, most preferably 1.9 to 2.1M.

In an embodiment, the glycine concentration in the $2^{nd}$ glycine precipitation in step (b) is 0.2 to 1.2M, preferably 0.3 to 1.1M, most preferably 0.5 to 0.9M.

In an embodiment, the glycine concentration in the $3^{rd}$ glycine precipitation in step (c) is 1.5 to 2.5M, preferably 1.8 to 2.3M, most preferably 1.9 to 2.2M.

The dissolution buffer used for dissolving the precipitate in steps (b) and (d) may be a dissolution buffer used commonly in the art to which the present disclosure pertains, and the dissolution of the precipitate may be performed using a buffer containing preferably 10 to 100 mM, more preferably 30 to 70 mM of sodium citrate at pH 6.0 to 9.0, preferably 7.0 to 8.0, most preferably 7.5.

In an embodiment, the glycine precipitation and the recovery of the precipitate may be performed by adding a suitable concentration of glycine in each step, and stirring with 200 to 1,000 rpm at 4 to 30° C., followed by centrifugation under 3,000 to 10,000 rpm at 4 to 25° C., but the scope of the present disclosure is not limited thereto.

In addition, the nanofiltration in step (d) may be performed using a commercially-available nanofiltration system, and the type of the filter that can be used in the present disclosure is preferably SV4 20N from Pall Corporation or Planova 20N from Asahi Kasei Co., Ltd., but is not limited thereto, and may be performed using a suitable buffer. Preferably, a buffer containing 10 to 30 mM sodium citrate, 50 to 150 mM NaCl, 1 to 7%, preferably 2 to 5% arginine at pH 6.0 to 9.0, preferably 7.0 to 8.0, most preferably 7.2 to 7.8 might be used. The nanofiltration in step (d) may performed at 20 to 37° C., preferably 28 to 35°, most preferably 25 to 35° under a pressure of 1 to 2 bar when using SV4 20N and 0.5 to 1 bar when using Planova 20N.

Preferably, the fibrinogen-containing solution of step (a) may be obtained by a process comprising the steps as follows, but is not limited thereto:

(i) dissolving a fibrinogen-containing cryopaste using a dissolution buffer to obtain a solution;

(ii) adding an adsorbent to the solution, thereby removing impurities by adsorption; and (iii) inactivating viruses, contained in the cryopaste, by solvent/detergent (S/D) treatment.

The cryopaste in step (i) may be dissolved using the dissolution buffer at a volume ratio of 1:2 to 1:6, preferably 1:3 to 1:5, most preferably 1:4. The dissolution buffer in step (i) may be a buffer containing 10 to 30 mM, preferably 20 mM sodium citrate, 50 to 150 mM, preferably 100 mM NaCl, and 50 to 150 mM, preferably 100 mM glycine, but is not limited thereto.

In addition, the adsorbent used in step (ii) is preferably aluminum hydroxide ($Al(OH)_3$), but is not limited thereto. The $Al(OH)_3$ adsorption gel which is an impurity-adsorbed adsorption precipitate may be removed from centrifugation. The adsorbent, aluminum hydroxide may have a concentration of 1.0 to 5.0%, preferably 1.5 to 3.0%, most preferably 2.0%, and may be used in an amount of 0.05 to 0.5 wt %, preferably 0.07 to 0.3 wt %, most preferably 0.9 to 0.15 wt % based on the weight of the cryopaste.

In the solvent/detergent treatment of step (iii), any solvent and detergent may be used without limitations, as long as they have the capability to inactivate viruses, particularly lipid enveloped viruses. The detergent may be selected from the group consisting of non-ionic and ionic detergents and is preferably selected to be substantially non-denaturing. Particularly, a non-ionic detergent is preferable in terms of removal convenience, and the solvent is most preferably tri-n-butyl phosphate (TNBP) as disclosed in U.S. Pat. No. 4,764,369, but is not limited thereto.

Preferably, the solvent/detergent treatment of step (iii) may be performed using a solvent/detergent solution containing a non-ionic detergent and tri-n-butyl phosphate (TNBP). The virus-inactivating agent that is used in the present disclosure is preferably a mixture of TNBP and at least one selected from among polysorbate 80 (Tween 80), polysorbate 20 (Tween 20), Triton X-100, and Triton X-45, but is not limited thereto.

The preferred solvent/detergent mixture is added for the concentration of TNBP in the fibrinogen-containing solution to be 0.2 to 0.6 wt %, preferably 0.24 to 0.36 wt %, and for the concentration of Tween 80 to be 0.5 to 1.5 wt %, preferably 0.8 to 1.2 wt %.

In addition, the method of the present disclosure may further comprise, between steps (c) and (d), step (c') of dissolving the precipitate recovered in step (c) in dissolution buffer to obtain a solution, precipitating the solution by adding glycine thereto for a glycine concentration to be identical to the glycine concentration of step (a), to obtain a precipitate ($4^{th}$ glycine precipitation).

The method of the present disclosure may optionally comprise, after the nanofiltration of step (d), (e) ultrafiltration/diafiltration (UF/DF) or ultrafiltration step; and/or (f) formulation step.

As used herein, "diafiltration" refers a technique that removes or collects any component (e.g., particles) from a target substance (solution) using a permeable filter capable of achieving separation according to the molecular weight (molecular size) of the component, thereby increasing the purity of the target substance. The ultrafiltration/diafiltration (UF/DF) in step (e) may be performed using a typical UF/DF system, and may comprise a change to a constant osmotic pressure, an exchange of a buffer, and an adjustment of the concentration of the buffer.

The term "fibrinogen" preferably refers human fibrinogen which can be purified, for example, from a mixture which contains fibrinogen and has been obtained from human blood. The phrase "mixture obtained from blood" refers, for example, whole blood, blood plasma, plasma fractions or plasma precipitates. Fibrinogen from human plasma or cryoprecipitate, particularly fibrinogen from Cohn fraction 1, is preferred. Fibrinogen can be isolated both from pooled plasma donations and from individual donations.

Human fibrinogen can also be obtained from the body fluids (e.g., milk) of transgenic animals (U.S. Pat. No. 5,639,940) or by recombinant expression from cell culture (U.S. Pat. No. 6,037,457). In addition, fibrinogen can be isolated from the appropriate fermentation supernatants or fractions produced therefrom. Meanwhile, fibrinogen can be isolated from animal blood containing fibrinogen, preferably blood derived from mammals (e.g., pigs, horses, cows, goats, sheep, and dogs).

Impurities or insoluble proteins in the present disclosure refer all proteins which occur in plasma other than fibrinogen or appear in the body fluids (e.g., milk) of transgenic animals or in the cell culture supernatant, and preferably, fibrinogen-degrading proteins which are able to degrade fibrinogen by proteolysis, or precursors of fibrinogen-degrading proteins (proenzymes) which must be previously activated for proteolytic degradation of fibrinogen, or activators of fibrinogen-degrading proteases, and fibrinogen degradation fragments having low molecular weights might be included.

The phrase "fibrinogen-containing cryopaste" refers a fibrinogen-containing cryoprecipitate derived from the above-described animals (preferably humans).

In the present disclosure, the "pH" of a solution (e.g., dissolved solution) measures the acidity or alkalinity relative to the ionization of a water sample. The pH of water is neutral, i.e., 7. Most pH readings range from 0 to 14. Solutions with a higher [H+] than water (pH less than 7) are acidic; solutions with a lower [H+] than water (pH greater than 7) are basic or alkaline. pH can be measured using a pH meter. pH of buffer may be adjusted using an acid or base such as HCl or NaOH. The dissolution buffer used in the present disclosure is preferably in the neutral pH range.

As used herein, the term "purification" can be interchangeably used with the term "clarification" and refers re-dissolving a precipitate or the like using a buffer, and then removing impurities from the solution resulting from the re-dissolution.

The fibrinogen purified by the method of the present disclosure has a purity of at least 90%, preferably at least 93%, most preferably at least 98%. Particularly, the produced fibrinogen protein in the present disclosure may be a fibrinogen protein having a purity of at least 98%.

EXAMPLES

Hereinafter, the present disclosure will be described in further detail with reference to examples. It will be obvious to a person having ordinary skill in the art that these examples are for illustrative purposes only and are not to be construed to limit the scope of the present disclosure.

Example 1: Process for Dissolution of Fibrinogen-Containing Cryopaste and Treatment with Al(OH)$_3$ Gel 1) 4 L of dissolution buffer (containing 50 mM sodium citrate at pH 7.5, 100 mM sodium chloride (NaCl), and 100 mM glycine) for dissolving fibrinogen-containing cryopaste was placed in a jacketed beaker, and then stirred at a controlled circulator temperature of 37° C. for 30 minutes or more. At this time, the temperature of the buffer was maintained at 37° C.

2) 1 kg of fibrinogen-containing cryopaste was added to 4 L of the dissolution buffer (fibrinogen-containing cryopaste:dissolution buffer=1 kg:4 L), and then stirred at a controlled stirrer speed of 150 rpm at 37° C. for 2 hours.

3) The fibrinogen-containing cryopaste solution was controlled to a temperature of 20 to 25° C., and then 150 g of aluminum hydroxide (Al(OH)$_3$) was added per kg of the fibrinogen-containing cryopaste (preferably, 2% aluminum hydroxide was added at a proportion of 0.5% by weight), followed by stirring at a controlled stirrer speed of 150 rpm at 20 to 25° C. for 1 hour.

4) After completion of the reaction, centrifugation was performed at 4000 rpm at 15° C. for 30 minutes.

5) After completion of the centrifugation, the supernatant was filtered through the Opticap XL2 Polysep II filter (Merck Millipore).

Virus Inactivation Process: Solvent/Detergent (S/D) Treatment 55.7 mL of virus inactivation solution (1% Tween 80, 0.3% TNBP (tri-N-butyl phosphate)) was added per 1 L of the filtered fibrinogen-containing cryopaste solution, followed by stirring at 150 rpm at 25° C. for 1 hour.

As a result, a solution in which putative virus components were inactivated was obtained by treating the filtered fibrinogen-containing cryopaste solution with solvent/detergent (S/D).

Example 2: 1$^{st}$ Glycine Precipitation Process

1) To the putative virus component-inactivated, filtered fibrinogen-containing cryopaste solution of Example 1, glycine was added until a final concentration of the glycine concentration becomes 1.9 to 2 M. At this time, the glycine was added so that the protein content of the fibrinogen-containing cryopaste solution would be 20 to 30 mg/mL.

2) Stirring was performed at a controlled stirrer speed of 300 rpm at 4 to 25° C. for 90 minutes.

3) The stirred, glycine-added, fibrinogen-containing cryopaste solution of 2) was centrifuged at 4000 rpm at 15° C. for 30 minutes.

4) The supernatant was removed, and the precipitate (hereinafter referred to as 1$^{st}$ glycine precipitation precipitate) was weighed, and then freeze-stored at −70° C. or below.

Example 3: 2$^{nd}$ Glycine Precipitation Process 3-1: 2$^{nd}$ Glycine Precipitation Process (Conditions Under 20° C., 0.75M and 15 mg/mL)

1) To dissolve the freeze-stored 1$^{st}$ glycine precipitation precipitate of Example 2, dissolution buffer (50 mM sodium citrate, pH 7.5) was placed in a jacketed beaker, and then stirred at a controlled circulator temperature of 37° C. for 30 minutes or more. At this time, the temperature of the buffer was maintained at 37° C.

2) The freeze-stored 1$^{st}$ glycine precipitation precipitate of Example 2 was added to the dissolution buffer of 1), and then stirred at a controlled stirrer speed of 150 rpm at 37° C. for 90 minutes.

3) The stirred 1$^{st}$ glycine precipitation precipitate solution of 2) was filtered through the Opticap XL2 Polysep II filter (Merck Millipore).

4) The filtered 1$^{st}$ glycine precipitation precipitate solution of 3) was placed in a jacketed beaker, and then the temperature of the circulator was controlled to 20° C.

5) When the 1$^{st}$ glycine precipitation precipitate solution reached a predetermined temperature, glycine was added until a final concentration of the glycine concentration becomes 0.5 to 0.9M. At this time, the glycine as added so that the protein content of the 1$^{st}$ glycine-added precipitation precipitate solution would be 14 to 15 mg/mL.

6) Stirring was performed at 300 rpm for 90 minutes while the temperature of the circulator was maintained at 20° C.

7) The stirred, glycine-added 1$^{st}$ glycine precipitation precipitate solution of 6) was centrifuged at 4000 rpm at 15° C. for 30 minutes.

8) The precipitate of 7) was removed, and the amount of the supernatant (hereinafter referred to as 2$^{nd}$ glycine precipitation supernatant) was measured.

3-2: 2$^{nd}$ Glycine Precipitation Process (Conditions Under 25° C., 0.8 M and 20 mg/mL)

An experiment was performed in the same manner as described in Example 3-1, except that the following conditions were used: glycine concentration: 0.8M; temperature: 25° C.; and protein concentration: 19 to 20 mg/mL.

3-3: 2$^{nd}$ Glycine Precipitation Process (Conditions Under 15° C., 0.8M and 10 mg/mL)

An experiment was performed in the same manner as described in Example 3-1, except that the following conditions were used: glycine concentration: 0.8M; temperature: 15° C.; and protein concentration: 9 to 10 mg/mL.

3-4: 2$^{nd}$ Glycine Precipitation Process (Conditions Under 15° C., 0.5M and 20 mg/mL)

An experiment was performed in the same manner as described in Example 3-1, except that the following conditions were used: glycine concentration: 0.5M; temperature: 15° C.; and protein concentration: 19 to 20 mg/mL.

Example 4: 3$^{rd}$ Glycine Precipitation Process

1) The temperature of the circulator was controlled to 20° C. When the temperature of the 2$^{nd}$ glycine precipitation supernatant obtained in Example 3 reached 20° C., glycine was added to the supernatant until a final concentration of the glycine concentration becomes 2.1M.

In a comparative example, the 1$^{st}$ glycine precipitation precipitate obtained in Example 2 was dissolved in 50 mM sodium citrate (pH 7.5) buffer at 35° C. for 90 minutes. Thereafter, glycine was added to the solution until a final concentration of the glycine concentration becomes 2.1M.

2) Stirring was performed at 300 rpm for 90 minutes.

3) The stirred, glycine-added, 2$^{nd}$ glycine precipitation supernatant of 2) was centrifuged at 4000 rpm at 15° C. for 30 minutes.

4) The supernatant was removed, and the precipitate (hereinafter referred to as 3$^{rd}$ glycine precipitation precipitate) was weighed, and then freeze-stored at −30° C. or below.

Analysis of Sample Purity by SEC-LC

The purity of fibrinogen in the $3^{rd}$ glycine precipitation precipitate, subjected to the $2^{nd}$ glycine precipitation process, and the purity of fibrinogen in the $3^{rd}$ glycine precipitation precipitate not subjected to the $2^{nd}$ glycine precipitation process were measured by the following test method and compared with each other.

a. Sample solution preparation: the sample concentration was corrected to 2 mg/mL, and 200 μL of the sample was added to each LC vial.

b. Test conditions: a test was performed under the following conditions: flow rate: 0.5 mL/min; column temperature: room temperature (RT); injection volume: 20 μL; analysis time: 30 minutes; detection wavelength: UV 280 nm; and pump distribution: 100% isocratic.

c. Test Procedure:

1) In accordance with Waters HPLC operating instructions, an HPLC system was prepared.

2) A TSK-gel $G3000SW_{XL}$ column and a TSKgel SWXL guard column were disposed along the liquid flow direction.

3) Equilibration of column: a mobile phase was allowed to flow at a flow rate of 0.5 mL/min for at least 30 minutes, and when the equilibration on the chromatogram was reached, the flow was stopped.

4) Analysis was performed under the same conditions as the above-described test conditions.

Table 1 below shows the purity of fibrinogen obtained when the $2^{nd}$ glycine precipitation process was performed or not performed.

Figure 1:
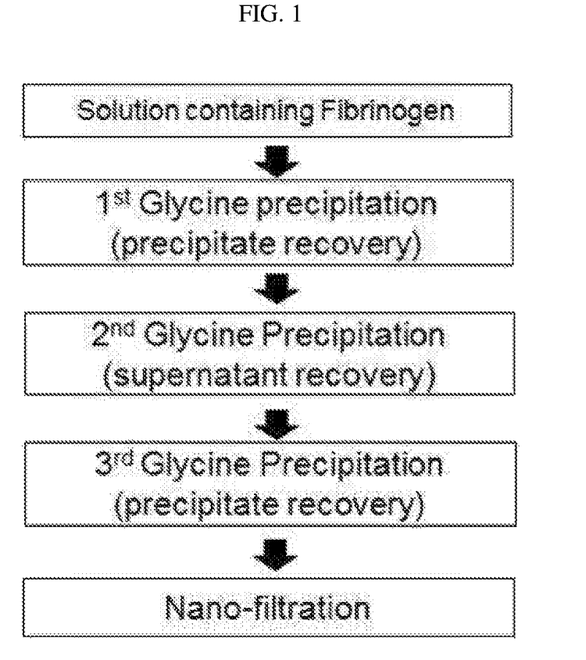
FIG. 1 shows a method for purifying fibrinogen according to the present disclosure.
Figure 2:
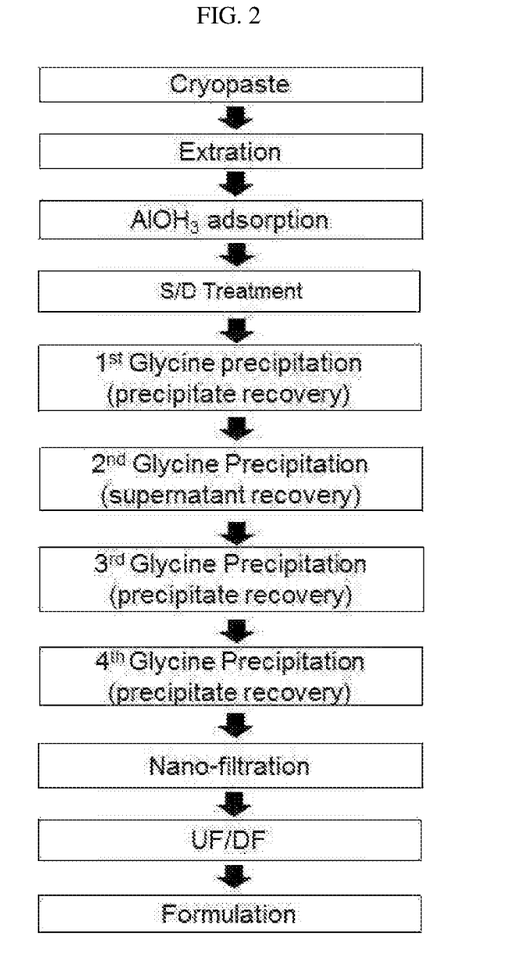
FIG. 2 shows a specific preparation method for formulating a fibrinogen product from cryopaste by use of a method for purifying fibrinogen according to the present disclosure.
Figure 3:
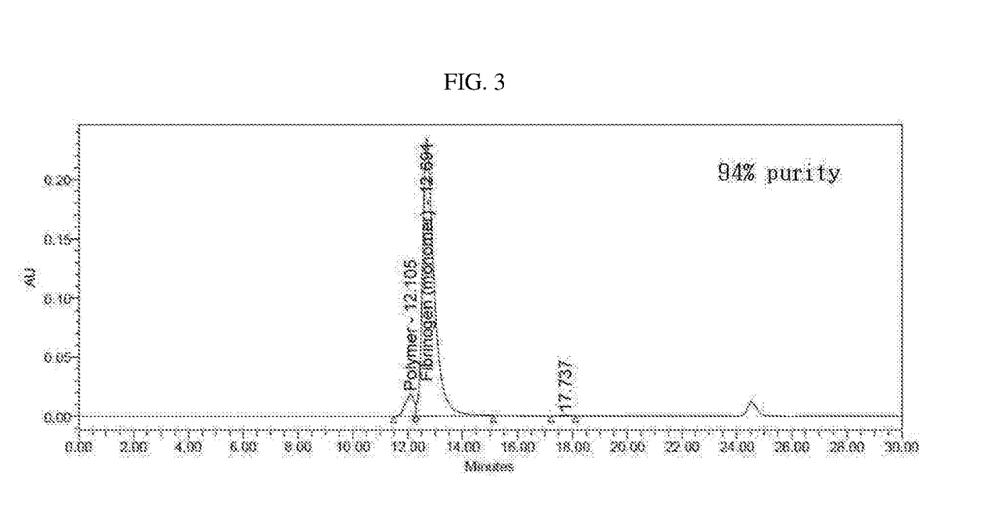
FIG. 3 shows the purity of fibrinogen obtained when performing only $1^{st}$ and $3^{rd}$ glycine precipitation processes without a $2^{nd}$ glycine precipitation process.
Figure 4:
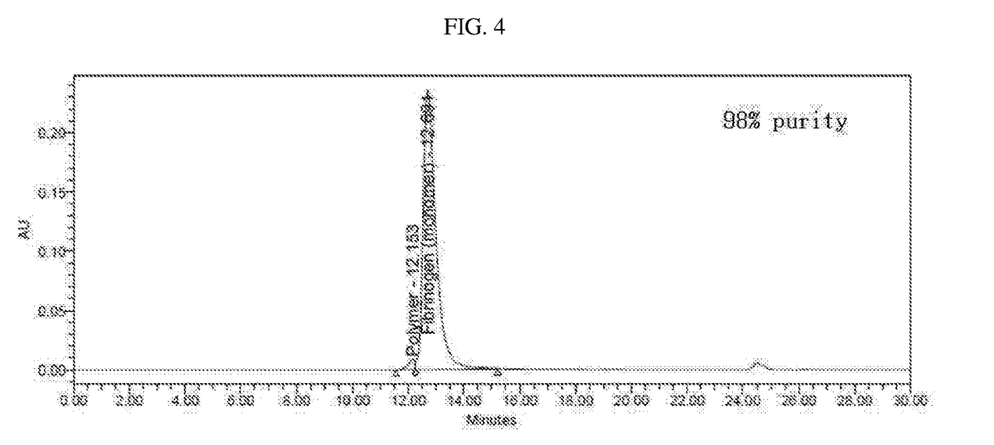
FIG. 4 shows the purity of fibrinogen obtained when performing all the $1^{st}$ to $3^{rd}$ glycine precipitation processes (under the conditions of 20° C., 0.75M and 15 mg/mL).
Figure 5:
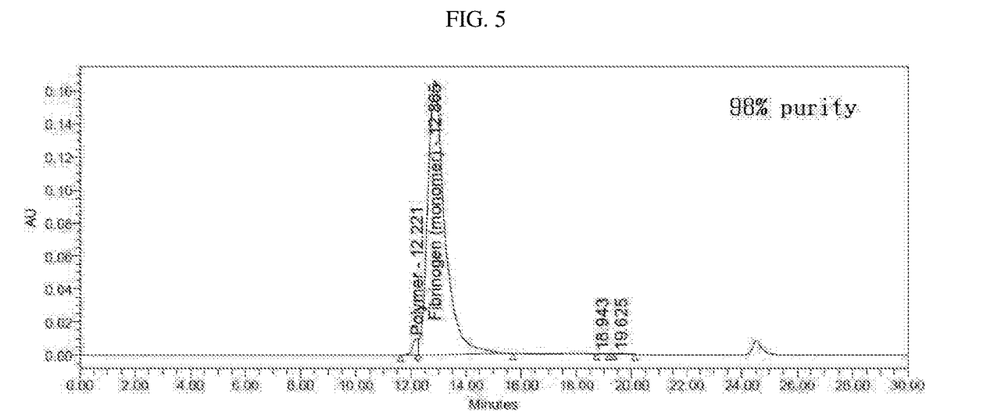
FIG. 5 shows the purity of fibrinogen obtained when performing all the $1^{st}$ to $3^{rd}$ glycine precipitation processes (under the conditions of 25° C., 0.8M and 20 mg/mL).
Figure 6:
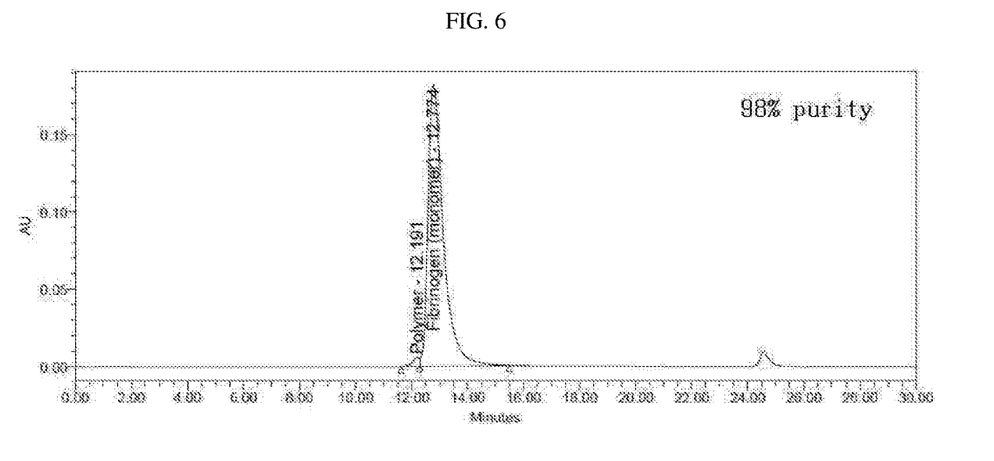
FIG. 6 shows the purity of fibrinogen obtained when performing all the $1^{st}$ to $3^{rd}$ glycine precipitation processes (under the conditions of 15° C., 0.8M and 10 mg/mL).
Figure 7:
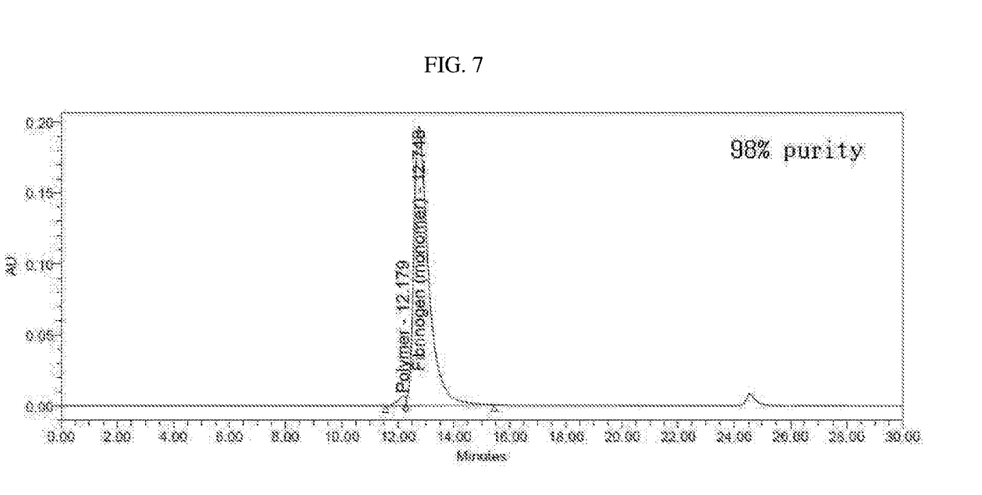
FIG. 7 shows the purity of fibrinogen obtained when performing all the $1^{st}$ to $3^{rd}$ glycine precipitation processes (under the conditions of 15° C., 0.5M and 20 mg/mL).

In addition, FIG. 3 shows the results obtained when performing only the $1^{st}$ and $3^{rd}$ glycine precipitation processes without the $2^{nd}$ glycine precipitation process, and FIGS. 4 (conditions of Example 3-1), 5 (conditions of Example 3-2), 6 (conditions of Example 3-3) and 7 (conditions of Example 3-4) shows the results obtained when performing all the $1^{st}$ to $3^{rd}$ glycine precipitation processes.

In summary, as shown in Table 1 below and FIGS. 3 to 7, when all the $1^{st}$ to $3^{rd}$ glycine precipitation processes were performed, the purity of the finally obtained fibrinogen was significantly high regardless of the conditions of the precipitation processes, compared to when only the $1^{st}$ and $3^{rd}$ glycine precipitation processes without the $2^{nd}$ glycine precipitation process were performed. Thus, it could be seen that when the precipitation processes are performed using glycine at lowered concentrations, the effect of removing impurities produced from the virus inactivation process is obtained.

TABLE 1

| No. | Purification method | polymer or impurity (%) | Fibrinogen (%) | Remarks |
|---|---|---|---|---|
| 1 | Examples 2 & 4 performed | 5.7 | 94.21 | Example 3 not performed |
| 2 | Examples 2, 3 & 4 performed | 1.96 | 98.04 | Example 3-1 performed |
| 3 | Examples 2, 3 & 4 performed | 1.64 | 98.25 | Example 3-2 performed |
| 4 | Examples 2, 3 & 4 performed | 1.33 | 98.67 | Example 3-3 performed |
| 5 | Examples 2, 3 & 4 performed | 1.77 | 98.23 | Example 3-4 performed |

Example 5: Optional $4^{th}$ Glycine Precipitation Process

It was shown that when the $1^{st}$ to $3^{rd}$ glycine precipitation processes as described in Examples 1 to 4 above were all performed, fibrinogen could be obtained with very high purity. In this Example, investigation was performed to determine whether, when an additional glycine precipitation process which is not an essential process was optionally performed, the purity of fibrinogen could be further increased.

1) To dissolve the freeze-stored $3^{rd}$ glycine precipitation precipitate of Example 4, dissolution buffer (50 mM sodium citrate (pH 7.5)) was placed in a jacketed beaker, and then stirred at a controlled circulator temperature of 37° C. for 30 minutes.

2) The freeze-stored $3^{rd}$ glycine precipitation precipitate of Example 4 was added to the buffer of 1), and then stirred at a controlled stirrer speed of 290 to 310 rpm at 30 to 35° C. for 90 minutes.

3) The temperature of the $3^{rd}$ glycine precipitation precipitate solution was lowered to 25° C., and glycine was added to the solution to a final concentration of 2.1M.

4) Stirring was performed at 300 rpm for 90 minutes while the temperature of the circulator was maintained at 25° C.

5) The stirred, glycine-added $3^{rd}$ glycine precipitation precipitate solution was centrifuged at 4000 rpm at 15° C. for 30 minutes.

6) The $4^{th}$ glycine precipitation precipitate of 5) was recovered, weighed, and then freeze-stored at −30° C. or below.

Example 6: DoE Experiment on Nano-Filtration Process 1) 250 mg or more of the $3^{rd}$ or $4^{th}$ glycine precipitation precipitate obtained in Example 4 or 5 was prepared.

2) Dissolution buffer (containing 20 mM sodium citrate at pH 7.5, 100 mM sodium chloride (NaCl), and 1 to 6% arginine) was added to the $3^{rd}$ or $4^{th}$ glycine precipitation precipitate, and the precipitate was dissolved by stirring at room temperature (20 to 25° C.) for 2 hours so that the final protein concentration would be about 3 mg/mL.

3) The concentration of the dissolved $4^{th}$ glycine precipitation precipitate of 2) was measured at an UV wavelength of 280 nm, and then the precipitate was diluted to a concentration of 0.7-3 mg/mL by use of dissolution buffer (containing 20 mM sodium citrate at pH 7.5, 100 mM sodium chloride (NaCl), and 1 to 6% arginine), and the final concentration was measured at a UV wavelength of 280 nm.

4) After correction of concentration, the sample was filtered through a bottle top filter (0.2 μm).

5) The filtered sample of 4) was filtered through a Pall 100N filter (10 $cm^2$ area) at room temperature (20 to 25° C.) and a pressure of 2 bar.

6) The filtered sample of 5) was filtered again through a Pall 50N (or Planova 35N) filter (10 $cm^2$ area). At this time, the filtration was performed under the conditions of room temperature (20 to 25° C.) and 2 bar (1 bar for Planova 35N).

7) The filtered sample of 6) was filtered through a Planova 20N (or SV4 20N) (10 $cm^2$ area). At this time, the filtration was performed under the conditions of 25 to 35° C. and 0.5 to 2 bar (Planova 20N: 0.5 to 1 bar; SV4 20N: 1 to 2 bar) (nano-filtration process time: 15 to 20 hours) (after Example 6 is performed, UF/DF as an additional process may be performed).

Table 2 below shows the efficiency and recovery rate of the Planova 20N and SV4 20N filter, obtained when the $2^{nd}$ glycine precipitation process was performed or not performed.

TABLE 2

|  | Planova 20N (Asahi) | | Pall SV4 20N (Pall) | |
| --- | --- | --- | --- | --- |
|  | 94% Purity | 98% Purity | 94% Purity | 98% Purity |
| Efficiency of filter (g/m$^2$) | 105.4 | 203.8 | 145.9 | 451.2 |
| Recovery of filter (%) | 76.1 | 92.3 | 90.5 | 92.1 |

Figure 8:
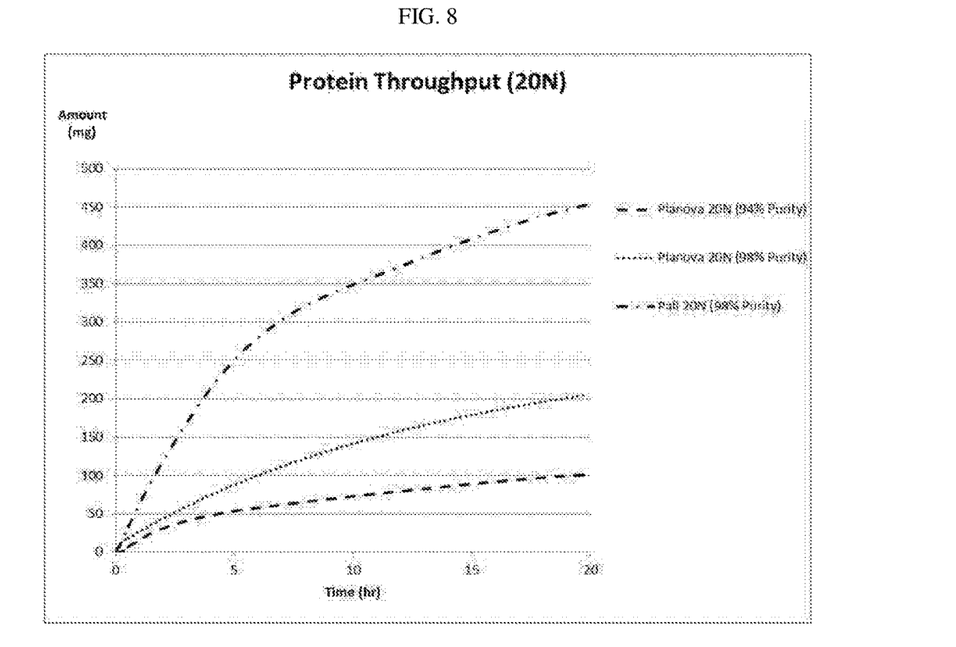
FIG. 8 shows the amount of fibrinogen filtered through a Planova 20N filter after a $2^{nd}$ glycine precipitation process was performed or not performed.

As a result, as shown in Table 2 above and FIG. 8, the purity of fibrinogen filtered through the nano-filter was compared between cases that the 2$^{nd}$ glycine precipitation process was performed and not performed as described in Example 3. As a result of the comparison, it was shown that when the 2$^{nd}$ glycine precipitation process was performed, the recovery of fibrinogen with a purity of 98% was high. Therefore, when the precipitation processes are performed using glycine at lowered concentrations, the effects of removing impurities produced in the virus inactivation process and increasing the filtration efficiency of the nano-filter at least 2-fold were obtained.

INDUSTRIAL APPLICABILITY

The novel method for purifying fibrinogen protein according to the present disclosure is a highly safe method that fundamentally blocks the entry of pathogenic components derived from animals (viruses). Furthermore, it can purify fibrinogen protein with high purity and high recovery rate by a simple process, and thus is very economical and efficient. In addition, fibrinogen purified by the method of the present disclosure has an advantage over fibrinogen purified by a conventional method in that it has higher purity, and thus has increased local activity, indicating that it can be effectively used for the prevention and treatment of blood-related diseases, particularly blood clotting diseases.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

The invention claimed is:

1. A method for purifying fibrinogen from a solution which contains fibrinogen and impurities, comprising the steps of:
(a) precipitating fibrinogen from the fibrinogen-containing solution by adding glycine to the solution to a concentration of 1.5 to 2.5 M glycine, and then removing a supernatant and recovering a first fibrinogen containing precipitate (1$^{st}$ glycine precipitation);
(b) dissolving the first fibrinogen containing precipitate of the 1st glycine precipitation of step (a) in a dissolution buffer to obtain a solution having a content of fibrinogen, precipitating the solution by adding glycine thereto to a concentration of 0.5 to 0.9 M glycine, and recovering a fibrinogen containing supernatant (2$^{nd}$ glycine precipitation);
(c) precipitating the supernatant of step (b) by adding glycine thereto to a concentration of 1.5 to 2.5 M glycine, and recovering a second fibrinogen containing precipitate (3$^{rd}$ glycine precipitation); and
(d) dissolving the second fibrinogen containing precipitate of step (c) in a dissolution buffer comprising 10-30 mM sodium citrate to obtain a diluted solution containing fibrinogen, and subjecting the diluted solution to nanofiltration using a nanofilter to obtain purified fibrinogen.

2. The method of claim 1, wherein the dissolution buffer used for dissolving the first fibrinogen containing precipitate in step (b) and the second fibrinogen containing precipitate in step (d) has a pH from 6.0 to 9.0.

3. The method of claim 1, wherein the nanofiltration in step (d) is performed at 20 to 37° C. under a pressure of 0.5 to 2.5 bar.

4. The method of claim 1, wherein the fibrinogen-containing solution of step (a) is obtained by a process comprising the steps of:
(i) dissolving a fibrinogen-containing cryopaste in a dissolution buffer to obtain a fibrinogen-containing solution;
(ii) adding an adsorbent to the fibrinogen-containing solution, thereby removing impurities by adsorption; and
(iii) inactivating viruses, contained in the cryopaste, by solvent/detergent treatment.

5. The method of claim 4, wherein the cryopaste in step (i) is dissolved in the dissolution buffer at a volume ratio of 1:2 to 1:6.

6. The method of claim 4, wherein the dissolution buffer in step (i) is a buffer comprising 20 mM sodium citrate, 100 mM NaCl, and 100 mM glycine.

7. The method of claim 4, wherein the adsorbent used in step (ii) is aluminum hydroxide (Al(OH)$_3$).

8. The method of claim 7, wherein the aluminum hydroxide is used in an amount of 0.05 to 0.5 wt % based on the weight of the cryopaste.

9. The method of claim 4, wherein the solvent/detergent treatment of step (iii) is performed using a solvent/detergent solution comprising a non-ionic detergent and tri-n-butyl phosphate (TNBP).

10. The method of claim 9, wherein the non-ionic detergent is at least one selected from the group consisting of polysorbate 80 (Tween 80), polysorbate 20 (Tween 20), Triton X-100, and Triton X-45.

11. The method of claim 1, further comprising, between steps (c) and (d), a step (c') dissolving the second fibrinogen containing precipitate recovered in step (c) in a dissolution buffer to obtain a solution, precipitating the solution by adding glycine thereto to a glycine concentration identical to the glycine concentration of step (a), to obtain a fibrinogen containing precipitate (4$^{th}$ glycine precipitation) for dissolution according to step (d).

12. The method of claim 1, further comprising, after the nanofiltration of step (d), at least one step selected from among (e) ultrafiltration/diafiltration step; and (f) formulation step.

13. The method of claim 1, wherein the purified fibrinogen has a purity of about 98% or higher.

\* \* \* \* \*